US008629986B2

(12) United States Patent
Hillmer et al.

(10) Patent No.: US 8,629,986 B2
(45) Date of Patent: Jan. 14, 2014

(54) OPTICAL FILTER AND METHOD FOR THE PRODUCTION OF THE SAME, AND DEVICE FOR THE EXAMINATION OF ELECTROMAGNETIC RADIATION

(75) Inventors: Hartmut Hillmer, Kassel (DE); Wolfgang Koecher, Kassel (DE); Juergen Krieg, Ettlingen (DE); Carl Sandhagen, Kassel (DE); Hardy Hoheisel, Baunatal (DE); Winfried Willemer, Bovenden (DE)

(73) Assignee: Biozoom Technologies, Inc., Agoura Hills, CA (US)

( * ) Notice: Subject to any disclaimer, the term of this patent is extended or adjusted under 35 U.S.C. 154(b) by 676 days.

(21) Appl. No.: 12/376,690

(22) PCT Filed: Aug. 9, 2007

(86) PCT No.: PCT/EP2007/007075
§ 371 (c)(1),
(2), (4) Date: Jun. 14, 2010

(87) PCT Pub. No.: WO2008/017490
PCT Pub. Date: Feb. 14, 2008

(65) Prior Publication Data
US 2011/0043823 A1    Feb. 24, 2011

(30) Foreign Application Priority Data

Aug. 9, 2006 (DE) .......................... 10 2006 039 071
Aug. 9, 2006 (DE) .......................... 10 2006 039 073

(51) Int. Cl.
*G01B 9/02* (2006.01)

(52) U.S. Cl.
USPC ........................................................ 356/519

(58) Field of Classification Search
USPC .................................................. 356/519, 454
See application file for complete search history.

(56) References Cited

U.S. PATENT DOCUMENTS 4,822,998 A * 4/1989 Yokota et al. ................. 250/226
(Continued)

FOREIGN PATENT DOCUMENTS

| DE | 19638693 A | 4/1998 |
|---|---|---|
| EP | 1286287 A | 2/2003 |
| WO | 9517690 A | 6/1995 |

OTHER PUBLICATIONS

Correia, J et al, "Single-chip CMOS optical microspectrometer" *Sensors and Actuators 82*, Delft Univ. of Technology Nov. 1999.
(Continued)

*Primary Examiner* — Tarifur Chowdhury
*Assistant Examiner* — Jonathan Hansen
(74) *Attorney, Agent, or Firm* — Norman B. Thot

(57) ABSTRACT

The invention relates to an optical filter and a method for its production, and to a device for the examination of the spectral and spatial distribution of an electromagnetic radiation irradiated from an object. The invention is based on the task of providing an optical filter of the above described type that is inexpensive to produce, which can be used to detect a plurality of wavelengths, in which, however, tuning of the DBR mirrors by means of displacement is not necessary. Furthermore, a method for the production of such a filter is provided. According to a first aspect of the present invention this task is solved by a method for the production of an optical filter array having two DBR mirrors, and a cavity present between the same, comprising cavity sections having a plurality of different heights, each forming one Fabry Perot filter element, characterized by the following steps: applying a first DBR mirror onto a substrate, forming of a layer comprised of a cavity material on the DBR mirror, wherein this layer is equipped with a plurality of cavity sections forming the filter elements by means of utilizing a nanoimprint method, and applying the second DBR mirror on the cavity material having a structuring that is defined by the different heights of the cavity sections.

27 Claims, 14 Drawing Sheets

(56) References Cited

U.S. PATENT DOCUMENTS

Figure 1:
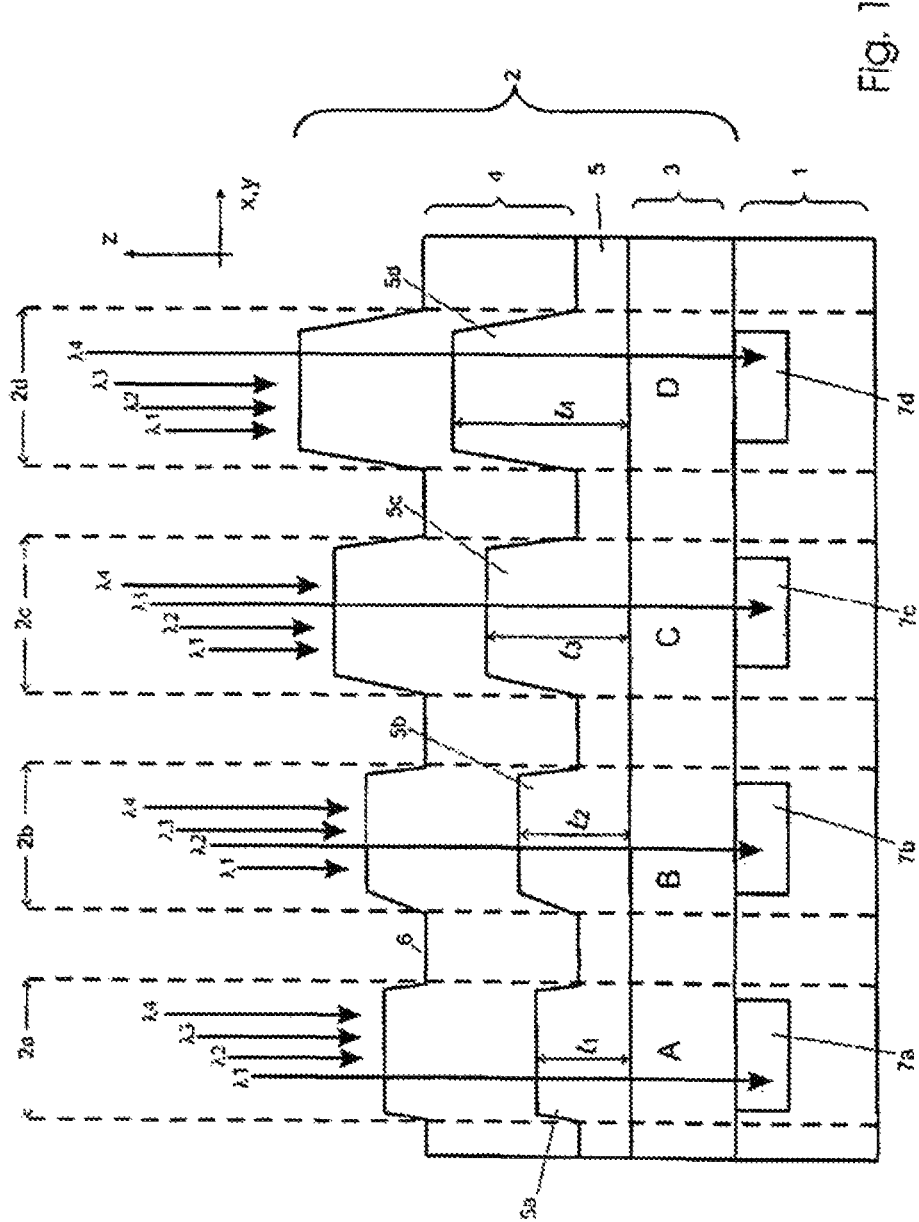

| | | |
|---|---|---|
| 5,144,498 A | 9/1992 | Vincent |
| 5,387,977 A | 2/1995 | Berg |
| 5,497,003 A | 3/1996 | Baliga |
| 5,568,186 A | 10/1996 | Althouse |
| 5,784,507 A | 7/1998 | Holm-Kennedy |
| 6,016,199 A | 1/2000 | Newton |
| 6,157,025 A | 12/2000 | Katagiri |
| 6,255,709 B1 | 7/2001 | Marso |
| 6,323,987 B1 | 11/2001 | Rinaudo |
| 6,462,876 B1 | 10/2002 | O'Brien |
| 6,482,742 B1 * | 11/2002 | Chou ............................ 438/690 |
| 6,998,613 B2 | 2/2006 | Syllaios |
| 7,179,654 B2 | 2/2007 | Verdonk |
| 7,310,153 B2 * | 12/2007 | Kiesel et al. .................. 356/519 |
| 7,330,266 B2 | 2/2008 | Guerineau |
| 7,399,421 B2 * | 7/2008 | Jacobowitz et al. ............ 216/24 |
| 7,426,040 B2 * | 9/2008 | Kim et al. ...................... 356/519 |
| 7,708,543 B2 * | 5/2010 | Shirotori et al. ............... 425/385 |
| 2008/0123097 A1 | 5/2008 | Muhammed |
| 2010/0316083 A1 * | 12/2010 | Chang-Hasnain et al. 372/50.11 |

OTHER PUBLICATIONS

Guo, Jay, "Recent Progress in nanoimprint technology and its applications" Dept. of Elec Eng. & Comp. Sci. Univ. of Mich. Ann Arbor stacks.iop.org/jphysD/37/R123 May 2004.

* cited by examiner

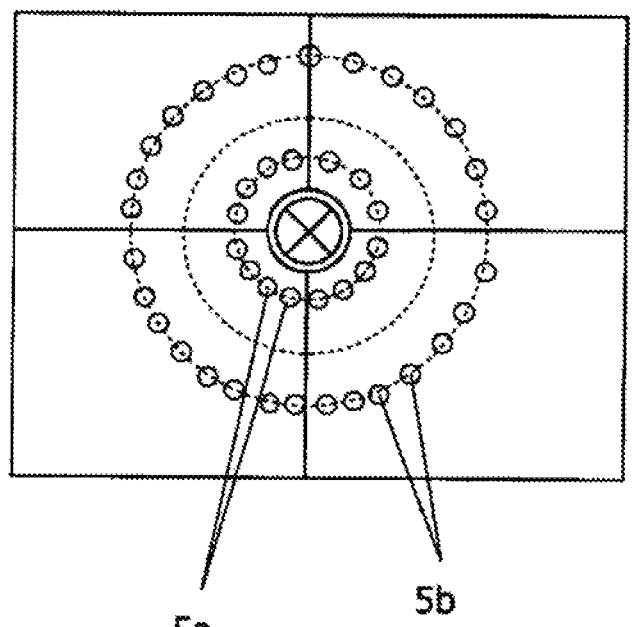
5a    5b    Fig. 11
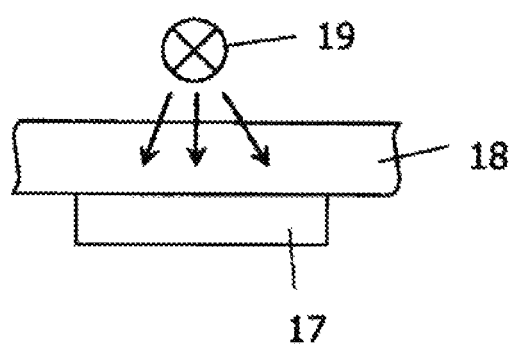
Fig. 12

OPTICAL FILTER AND METHOD FOR THE PRODUCTION OF THE SAME, AND DEVICE FOR THE EXAMINATION OF ELECTROMAGNETIC RADIATION

CROSS REFERENCE TO RELATED APPLICATIONS

This application is the US national phase of PCT application PCT/EP2007/007075, filed 9 Aug. 2006, published 14 Feb. 2008 as WO2008/017490, and claiming the priority of German patent application 102006039071.7 itself filed 9 Aug. 2006 and PCT patent application PCT/EP2007/007075 itself filed 9 Aug. 2006, whose entire disclosures are herewith incorporated by reference.

The invention relates to an optical filter and a process for its production, as well as to an apparatus for the examination of the spectral and local distribution of an electromagnetic radiation irradiated from an object.

For measurement technique, analytics, data storage, image storage and image processing, as well as generally for optical tele and data communication, optoelectronic components, in particular formed as optical filters, are frequently necessary, which can be tuned to several adjacent wavelengths. Filters of this kind, for example, consist of what is referred to as Fabry Perot filters, which have at least two DBR mirrors separated by a cavity (DBR=Distributed Bragg Reflector). Such filters are reflective in a wavelength range identified as a stopband, preset by their construction, however in a thin passband (=Dip) situated inside this stopband they are transmitting. The DBR mirrors for this purpose each contain at least one layer period that consists of two or more layers with different thicknesses and/or refractive indices. The number of layer periods is mostly integral, however, it can also be half-integral, e.g. if at the end of a stack formed by layer periods not all the layers of the respective period come to lie. By the number of layer periods and the refractive index contrast, the width of the stopband and the reflectivity profile in the stopband, and, by the optical length of the cavity, the location of the transmission band or the location of its central or dominant wavelength can be selected or determined. Finally, in Fabry Perot filters, it is possible to change the dominant wavelength of the transmission band within the tuning range preset by the stopband by changing the geometric and with it also the optical length of the cavity by shifting the two DBR mirrors in relation to each other. The component in this way can be tuned to one of several wavelengths $l1, l2 \ldots ln$.

Replacement Sheet (Rule 26)

Optical components of the kind described are commonly known (e.g. DE 103 18 767 A1). It is also known that their application results in the disadvantage that tuning the filter in the entire stopband is mostly not possible for constructive reasons, or it is associated with high technical effort. For avoiding this disadvantage, several filters with different electronic tuning ranges could be provided, but this would also be expensive. Apart from that, it is frequently undesirable to tune the filter by relatively shifting the DBR mirrors, in particular if it is to serve the purpose of determining or establishing the intensity at a defined wavelength in a radiation irradiated by a radiation source (e.g. light), with which wavelength of a multitude of possible wavelengths the radiation is currently irradiated by the radiation source.

Starting from here, the invention is based on the technical problem of proposing an optical filter of the type described above, which can be produced inexpensively and with which a multitude of wavelengths can be detected, wherein, however, tuning by shifting the DBR mirrors is not necessary. In addition, a process for the production of such a filter is to be proposed.

The present invention serves to solve this technical problem.

By the invention, an optical filter is advantageously created, which contains at least two filter elements, each of which has a characteristic transmission band. With particular advantage, the filter is additionally provided with a respective photoelectronic detecting device and connected with it to form an optoelectronic component made of one or two pieces. In this way not only the various filter elements of the filter, but also the photo elements necessary for detection or distinction of the transmission bands or for spectral evaluation of the incorporated radiation are integrated in one and the same component. It is possible to make visible the characteristic transmission bands and/or the spectral distribution of the absorbed radiation simply by querying the photo elements, i.e. without mechanical tuning of the filter. With particular advantage, a component is therefore proposed, which not only has two, but a multitude of filter elements with many different transmission bands. Such a component, when applying the method according to the invention, can be produced by relatively simple means, in particular if the filter elements are only distinguished by the thickness of their cavity layer and the filter is directly mounted on a substrate, which e.g. has a detecting device produced in CMOS technology.

Further advantageous characteristics of the invention result from the sub-claims.

The present invention also relates to an apparatus and to the application thereof.

In medicine, for non-invasive diagnostics and therapy control, the so-called remission spectroscopy is increasingly applied. As the intensity of the remission radiation emitted by a tissue, the skin or the like, as a rule depends on both the place and the spectral distribution, sensor or detecting devices are necessary, which enable both a local and a spectral resolution. The detecting devices available so far are not yet optimal for this purpose.

In television technology, e.g. CCD sensor arrays are known which consist of a multitude of image sensors or sensor elements and color filters applied on them. The color filters are e.g. produced from polymer films and filter elements introduced into them, which are sensitive to the colors red, blue, and green. For remission spectroscopy, such components are not or only partially suitable, due to the only three measurable spectral ranges.

In addition, in particular in tele and data communications, optoelectronic components with color filters in the form of Fabry Perot filters are used to each of which a photo element or the like is assigned (e.g. DE 103 18 767 A1). Such filters have at least two DBR mirrors separated by a cavity (DBR=Distributed Bragg Reflector) and are reflecting in a wavelength range called a stopband, preset by their construction, however, they are transmitting in at least one narrow transmission band (=Dip) situated inside this stopband. Filters of this type have the advantage that the transmission band can be changed within a tuning range preset by the stopband, by e.g. changing the geometric and with it also the optical length of the cavity by shifting the two DBR mirrors relative to each other. In this way, the component can, applying one single sensor element, be tuned to one of many wavelengths $l1, l2 \ldots ln$. However, this results in the disadvantage that no spatial resolution is enabled and tuning the filter in the entire stopband is mostly not possible for constructive reasons or it involves a high technical effort. For remission spectroscopy, such components are not very suitable either.

For remission spectroscopy in medicine, to this day devices of the kind indicated at the beginning are therefore mainly used, which contain a thin optical fibre as an element absorbing radiation, one end of which is placed on a tissue to be examined or e.g. on the human skin, and the other end of which leads to a spectrometer, which for examining the spectral intensity distribution of the remitted light is provided e.g. with a prism, a grid, or the like and a CCD camera downstream of it (e.g. Applied Optics, 1. June 1998, Vol. 37, no. 16, p. 3586 to 3593 or Applied Optics, 1. January 2002, Vol. 41, no. 1, p. 182 to 192). A spatial resolution in addition to the spectral resolution requires a multitude of such optical fibers and respective spectrometers or a spectrometer which is arranged for scanning a multitude of optical fibers one after the other. Both involves much expenditure and is therefore undesirable. It would be accordingly expensive to provide a single optical fibre and to move it over the areas to be scanned.

Based on this state of the art, the invention is based on the technical problem of shaping the apparatus of the kind indicated at the beginning in such a way that it enables a spatial resolution and a spectral resolution at the same time, without a movable component, a multitude of spectrometers or a tunable filter being necessary.

The specific characteristics of the present invention serve to solve this task.

By the invention, an apparatus is created, which in a common sensor unites both photovoltaic sensor elements and at least four, preferably however much more than four filter elements with different spectral transparency properties to each other. Specific spectrometers or the like and/or movable parts are thus no longer required. In fact, it is sufficient to place the sensor on the object to be examined, e.g. the human skin or a tissue, and to query the present photovoltaic sensor elements with electric means. Tuning the filter is not necessary. By each filter element, both a spectral information and a local information is received. In the presence of a large number of filter elements, which are each permeable for a different spectral range, in addition, due to the fact that more or less of the filter elements are united into a macropixel delivering the location information, the spatial resolution or the spectral resolution can alternatively be increased or diminished.

An aspect of the present invention is also to provide an apparatus.

Further advantageous characteristics of the invention result from the subclaims.

Figure 2:
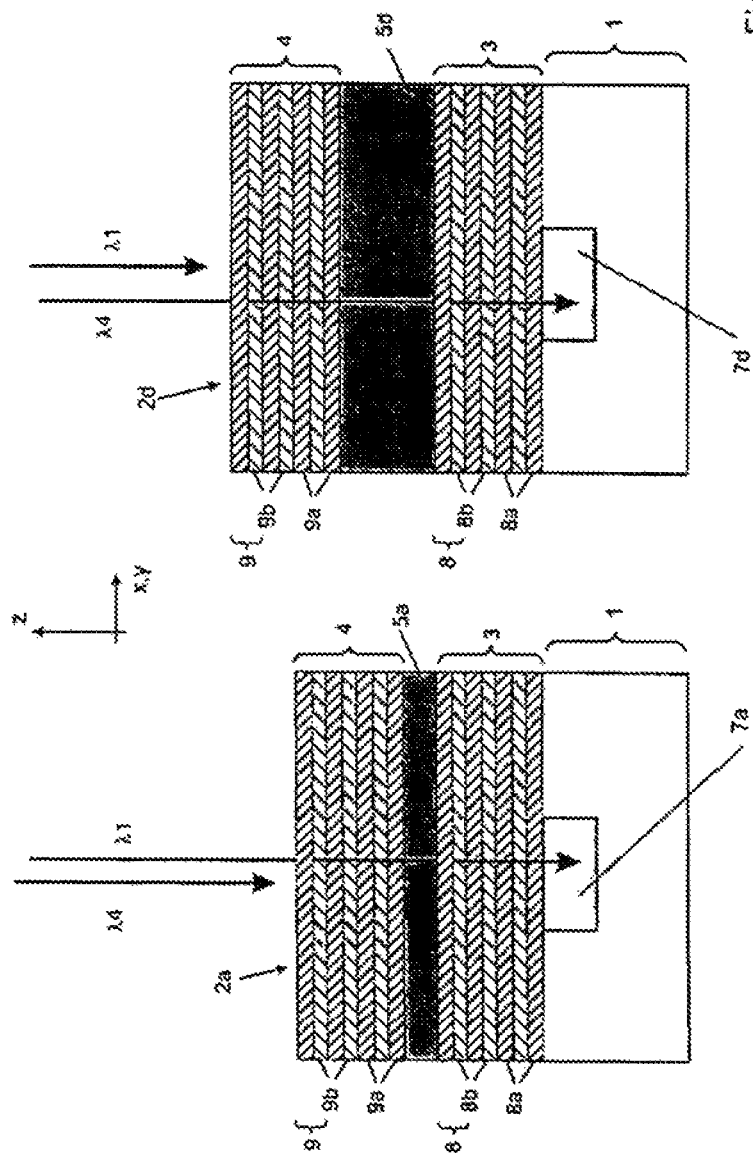
Figure 3:
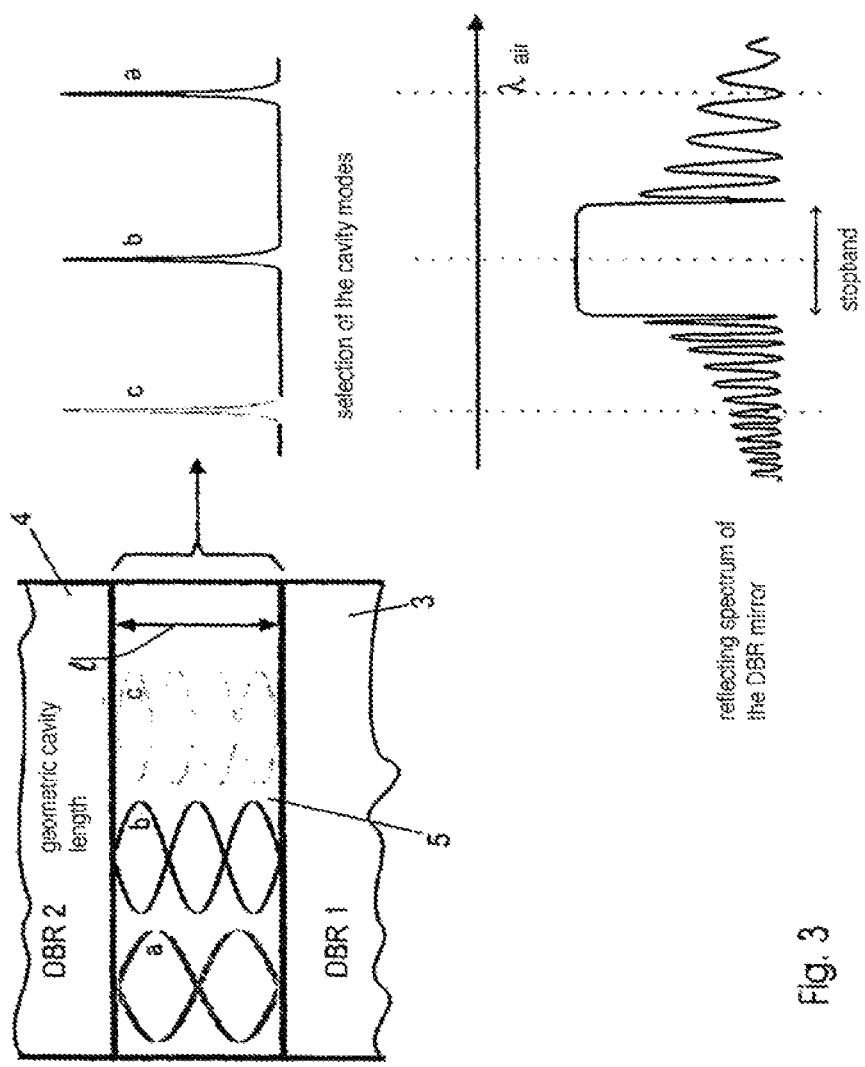
Figure 4:
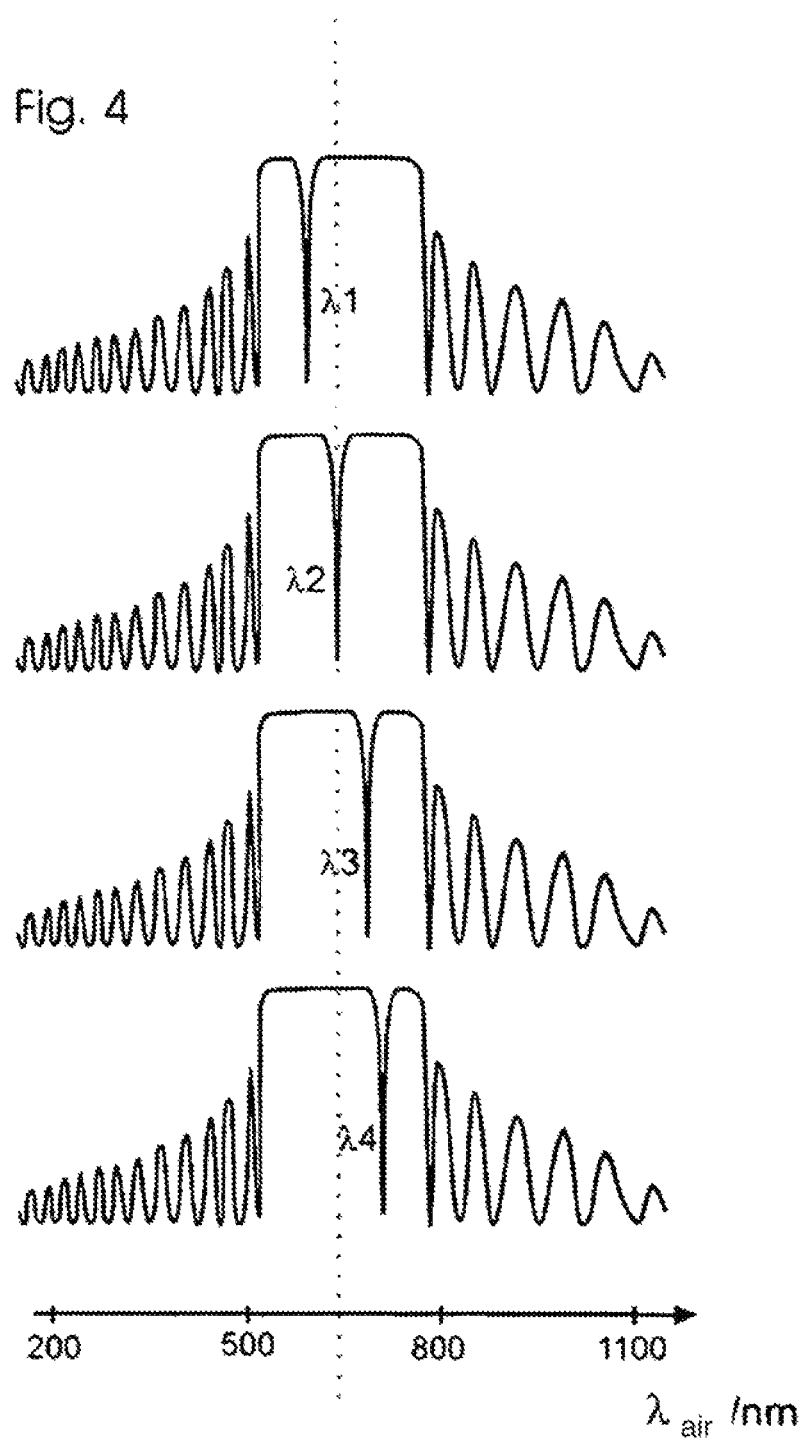
Figure 7:
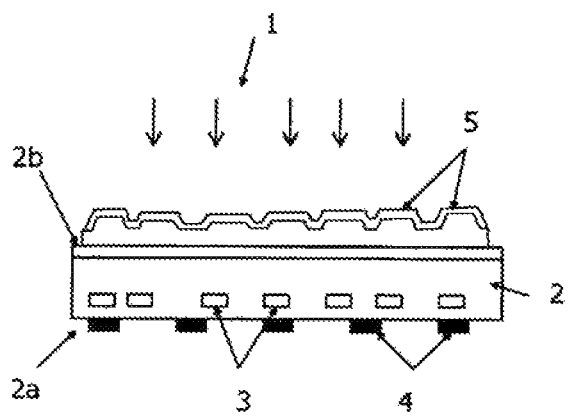
Figure 8:
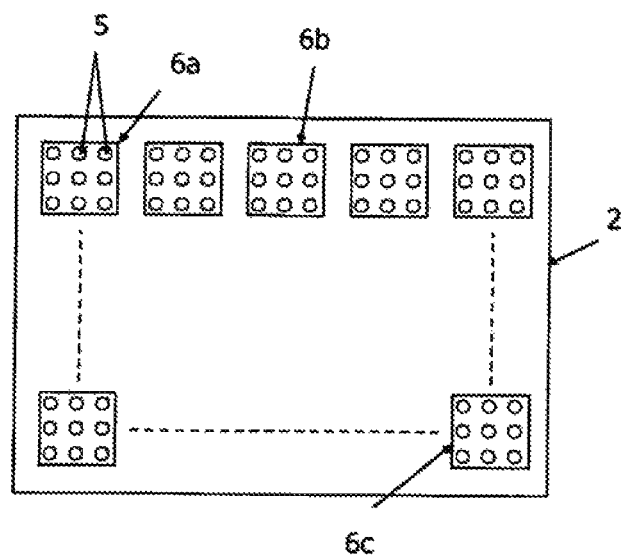
Figure 9:
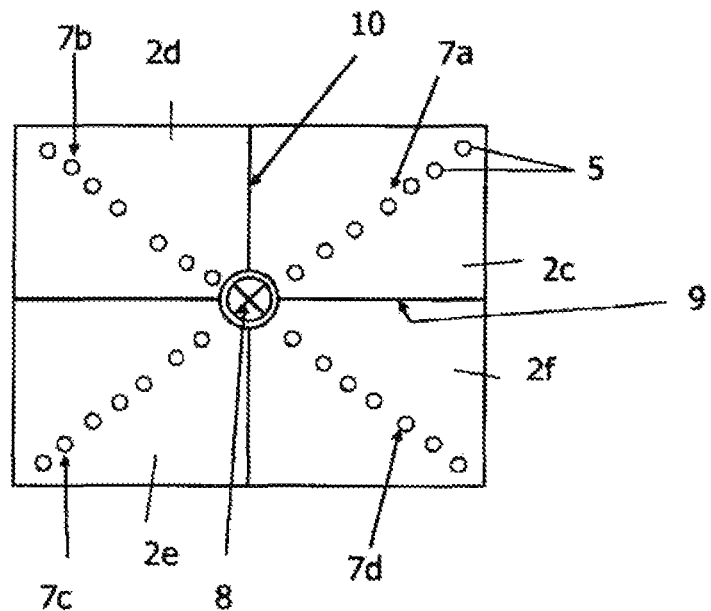
Figure 10:
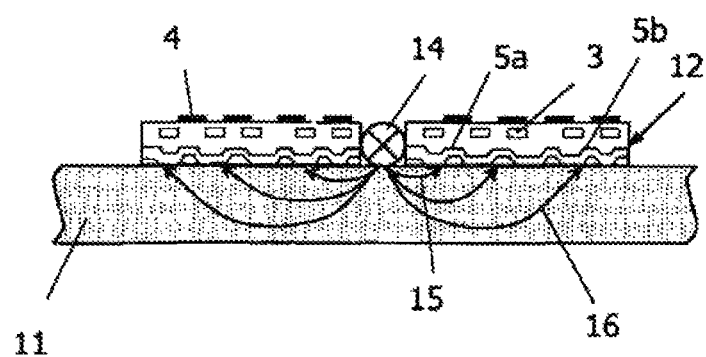
Figure 13:
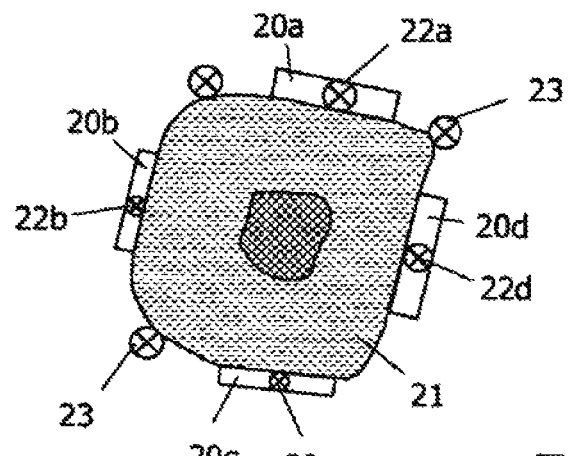
Figure 14:
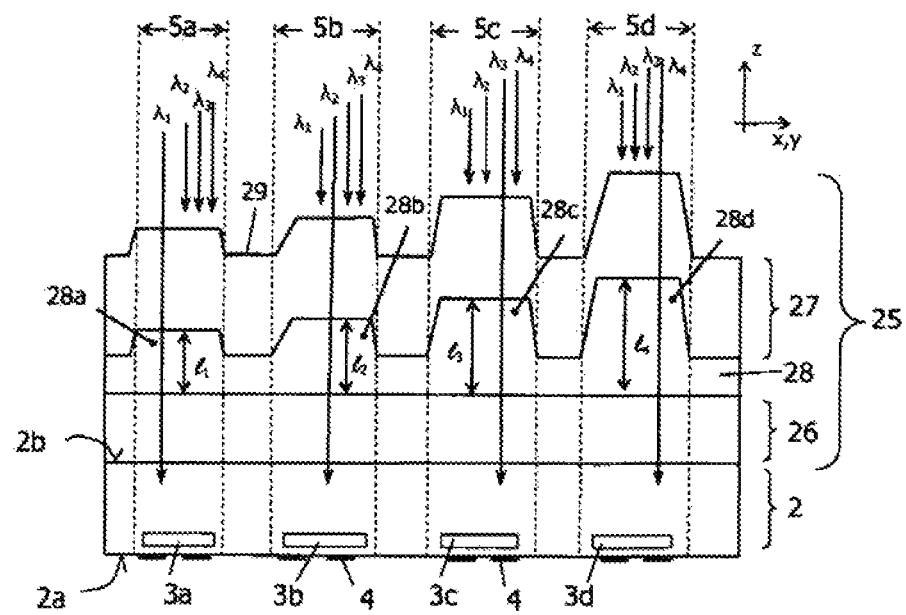

The invention is explained in more detail in the following in association with the drawings included, according to the embodiments. The FIGS. show:

FIG. 1 schematically the structure of an optical filter according to the invention with two DBR mirrors and a respective detecting device;

FIG. 2 a schematic longitudinal section through two filter elements of the filter according to FIG. 1, wherein the mirror curvature of an upper DBR mirror is not shown;

FIG. 3 schematically possible transmission bands of a Fabry Perot filter for a preset geometric length of the cavity;

FIG. 4 schematically and typically four transmission bands obtained with the filter according to FIG. 1; and FIGS. 5*a* to 5*c* and 6*a* to 6*c* schematically different steps of two embodiments for the production of the component provided with the detecting device according to FIG. 1;

FIG. 7 a rough schematic cross-section through an apparatus according to the invention for the examination of the spectral and local distribution of an electromagnetic radiation;

FIG. 8 a schematic top view on the apparatus according to the invention with a first embodiment for a possible arrangement of sensor and filter elements;

FIG. 9 a schematic top view on the apparatus according to the invention with a second embodiment for a possible arrangement of sensor and filter elements;

FIG. 10 a schematic cross-section through another embodiment of the apparatus according to the invention during its application for the examination of remission spectra;

FIG. 11 a top view on the apparatus according to FIG. 10;

FIG. 12 a schematic cross-section through another embodiment of the apparatus according to the invention during its application for the examination of transmission spectra;

FIG. 13 schematically the application of an apparatus according to the invention for tomography;

FIG. 14 the structure of an embodiment of a preferred apparatus according to the invention with two DBR mirrors and a respective sensor device.

Figure 15:
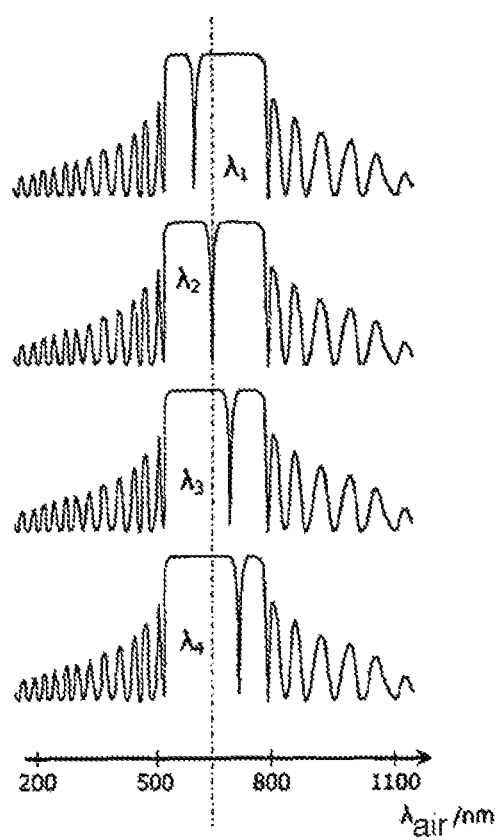

FIG. 15 schematically and typically transmission bands received with four filter elements of the apparatus according to FIG. 14.

Figure 16A:
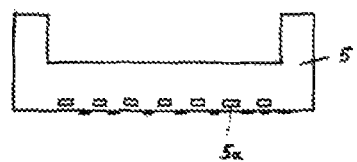
Figure 16B:
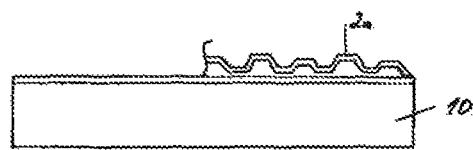
Figure 17:
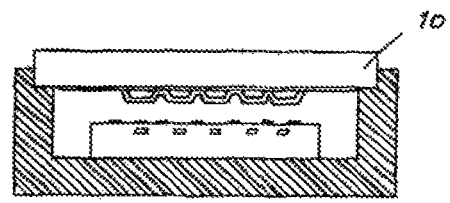

FIG. 16*a* and 16*b* a schematic embodiment for a possible arrangement of sensor and filter elements on separate substrates FIG. 17 a schematic cross-section of an apparatus according to the invention, in which the substrate of the filter device at the same time forms the window of the case of the optoelectronic component.

Figure 18:
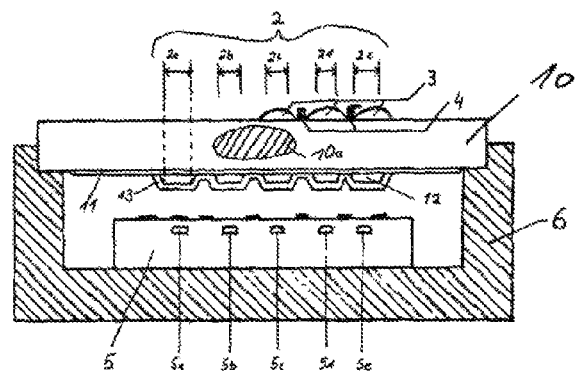
Figure 19:
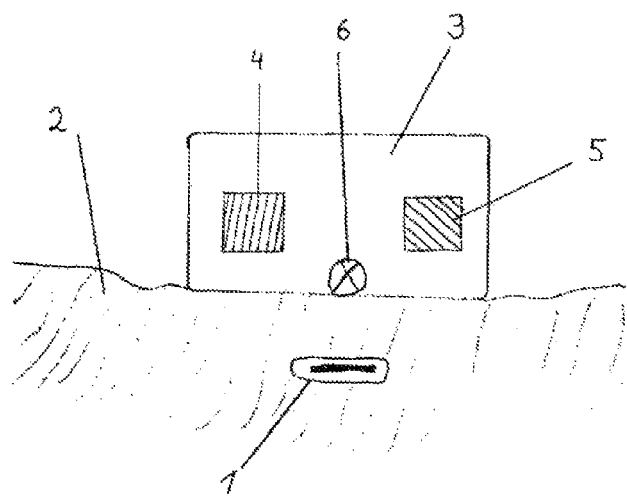
Figure 20:
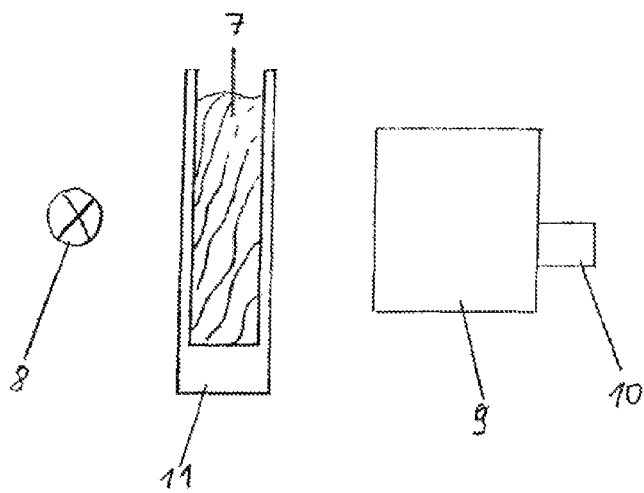
Figure 21:
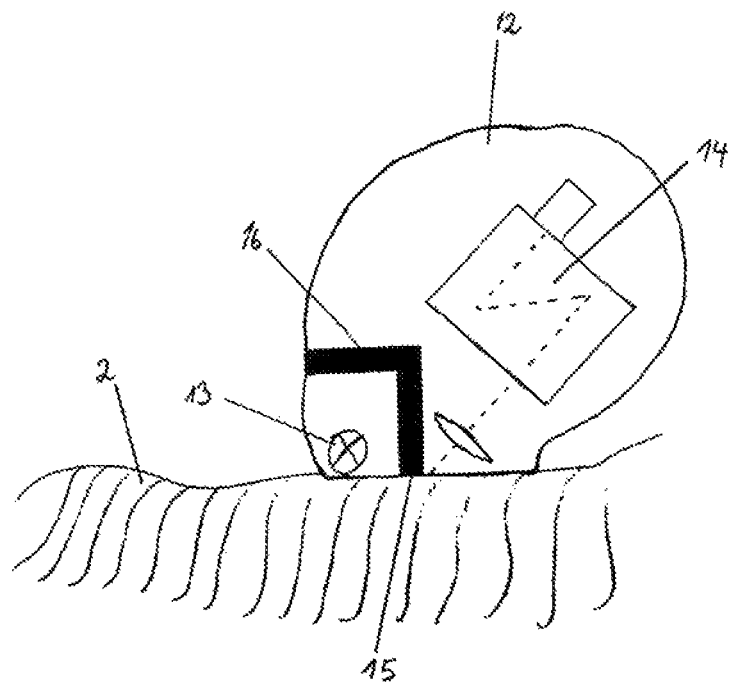
Figure 22:
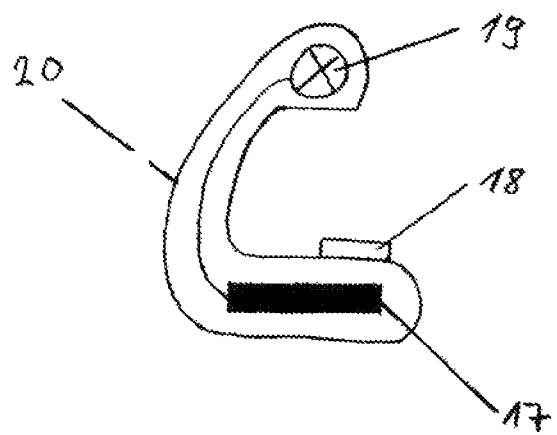

FIG. 18 schematically an embodiment for the complete or partial execution or arrangement of further optical functions in or to the window FIG. 19 schematically the application of an apparatus according to the invention for transmission or absorption measurement FIG. 20 schematically the arrangement which is replaced by the apparatus according to the invention FIG. 21 schematically another arrangement which is replaced by the apparatus according to the invention FIG. 22 a schematic cross-section through another embodiment of the apparatus according to the invention with an integrated light source According to FIG. 1, a component according to the invention, contains a substrate 1 consisting of e.g. silicon and an optical filter 2 arranged on it, as a whole provided with the reference sign 2. The filter 2 contains a first DBR mirror 3 resting on the substrate 1, a second DBR mirror 4, which is arranged on a side of the first DBR mirror 3 opposite to the substrate 1 and distanced from it, and a cavity provided between the two DBR mirrors 3 and 4, which is indicated in FIG. 1 as a whole with reference sign 5. The complete component therefore represents a multi-layered body substantially consisting of four layers located one above the other. All these layers substantially extend over the entire length running e.g. in the x direction of an imaginary Cartesian coordinate system and the entire width running e.g. in the y direction of the imaginary coordinate system of the component. Each layer forming the substrate 1 and each zone forming the first DBR mirror 3 continuously have substantially the same thickness perpendicular to the xy plane of the imaginary coordinate system, i.e. in z direction.

As FIG. 1 further shows, a layer of a material forming the cavity 5 is arranged on the first DBR mirror 3. This layer has a different thickness parallel to the z direction. Cavity 5 formed by the layer in particular has a comparatively small thickness in a section 5*a*, a slightly larger thickness in a section 5*b* and even larger thicknesses in sections 5*c* and 5*d*.

Geometric lengths 11 to 14 of the cavity 5 in these sections 5a to 5d therefore all have different values. Between sections 5a and 5d there are separating areas 6, in which the cavity material e.g. has a preset, constant thickness, and which spatially separate sections 5a to 5d of the cavity 5 from each other.

On the layer formed by the cavity material, there is a zone forming the second DBR mirror 4. This zone everywhere has the same thickness in FIG. 1—when observed in z direction. The bottoms and tops of this zone therefore have an outline or a structuring which corresponds to the upper outline or structuring of the cavity 5 in FIG. 1. The distance of the bottom and top of the DBR mirror 4 measured in z direction in FIG. 1 substantially is the same everywhere.

Due to the described conformation of the cavity 5, the filter 2 contains four filter elements 2a to 2d in this embodiment, as indicated in FIG. 1 by dashed lines, wherein each filter element 2a to 2d is formed by one of sections 5a to 5d of the cavity 5 and each by one respective section of the DBR mirrors 3 and 4. In the top view, i.e. in the xy plane, these filter elements 2a to 2d preferably have a circular shape, although they could in principle also have other peripheral contours.

Alternative to the above-described description, the component can have further filter elements, which are identical to the described filter elements 2a to 2d. This way, it would be possible e.g. to provide each filter element 2a to 2d twice in the component for redundancy reasons.

The substrate 1 is preferably a film which is translucent or diaphanous for the electromagnetic radiation to be detected, a thin glass top, a silicon wafer or the like, wherein "translucent" is understood to mean that the wafer does not necessarily need to be transparent in order to let through the light passing the filter 2 in an uninfluenced way, but can also have e.g. a scattering function and therefore be formed either altogether as a diffusing panel or be provided with means scattering the light.

In an embodiment particularly advantageous and perceived as the best so far, the component according to FIG. 1 is provided with a photoelectric detecting device, formed array-like, integrated into the substrate 1. It preferably contains one photo element 7a to 7d for each filter element 2a to 2d, e.g. in the form of a photo diode. The photo elements 7a to 7d are arranged in FIG. 1 in the substrate 1 in such a way that they are arranged directly under those sections of the DBR mirror 3 which are assigned to a respective filter element 2a to 2d. For example the photo element 7a is therefore assigned in such a way to the filter element 2a that it can only absorb the radiation let through by the filter element 2a. The same applies, mutatis mutandis, to the filter elements 2b to 2d and the respective photo elements 7b to 7d. For redundancy and other reasons, it can be expedient to arrange at least two identical photo elements 7a to 7d under each filter element 2a to 2d in such a way that if one of the two photo elements fails, the other remains effective, and/or to arrange selected photo elements 7a to 7d at the same time under at least two different filter elements 2a to 2d, so that they respond when one and/or the other filter element lets radiation through. How the photo elements 7a to 7d are assigned to each individual filter element 2a to 2d, per se is left to discretion and substantially depends on how the detection and/or evaluation of the radiations let through by the filter elements 2a to 2d, located in the transmission bands or their wavelengths, is to take place.

The substrate contains the photo elements 7a to 7d sensitive to radiation either close to the interface to the filter elements 2a to 2d, in the volume, or to its interface opposite of filter 2. The photo elements 7a to 7d can consist of phototransistors, photodiodes, photoconductors and CCD elements or the like, i.e. of any optional element which is suitable for detecting radiation within the range described here.

Finally, the substrate 1 preferably also contains a multitude of electrical components in the form of transistors and diodes or the like, by means of which the electrical signals 7d emitted by the photo elements 7a to 7d can be processed. For this purpose, a plate or film, produced in CMOS technology or the like, is expediently used as a substrate 1, also containing the photo elements 7a to 7d.

According to FIG. 1, the component therefore altogether consists of an optical filter 2, which has four filter elements 2a to 2d with identical DBR mirror sections, but different cavity sections 5a to 5d, and of a substrate 1 having a photoelectronic detecting device, carrying the filter 2, so that it forms a filter and sensor array produced in one piece in FIG. 1. If applying a material which continuously remains the same and therefore has the same refractive index n everywhere for cavity 5, the cavity sections 5a to 5d have optical lengths $L1=l_1 \cdot n$, $L2=l_2 \cdot n$, $L3=l_3 \cdot n$ and $L4=l_4 \cdot n$, which differ from each other by their geometric lengths $l_1$ to $l_4$.

Instead of the four filter elements 2a to 2d represented in FIG. 1, the component can also have only two or three or much more than four filter elements 2a to 2d and assigned photo elements 7a to 7d. The e.g. circular filter elements 2a to 2d and the respective photo elements 7a to 7d can be arranged bidimensionally and alternatively in lines and columns, which form, in a Cartesian or polar coordinate-like way, the lines and columns of a corresponding imaginary coordinate system (e.g. lines parallel to the x axis and columns parallel to the y axis). Alternatively, however, a one-dimensional arrangement in straight or curved lines or some other arrangement is also possible. In addition, the filter and photo elements 2a to 2d and 7a to 7d can also be arranged regardless of whether they are arranged line by line and/or column by column, with a regular or an irregular distribution.

FIG. 2 exemplifies details of the two sections involved in the formation of the filter elements 2a and 2d of the DBR mirrors 3 and 4. Both sections of the DBR mirror 3 in this embodiment have three and a half layer periods 8, wherein each period 8 contains a layer 8a and a layer 8b. As one layer 8a each borders both to the substrate 1 and to the cavity section 5a or 5d, three and a half layer pairs 8 are present in the embodiment. In an appropriate manner, the two sections shown in FIG. 2 of the DBR mirror 4 have three and a half layer periods 9 with layers 9a and 9b, which expediently correspond to the layers 8a, 8b, but can also be formed differently from them. The layers 8a, 9a and 8b, 9b for the rest differ in the usual way (cf. e.g. DE 103 18 767 A1 and the further printed materials indicated there) by their layer thickness and/or their refractive index, i.e. by their optical thickness. All the layers 8a, 9a can be formed equally or also differently among themselves. The same applies to layers 8b and 9b. In addition, the differences between the refractive indices of the layers 8a and 8b (or 9a and 9b), i.e. the refractive index contrasts, are e.g. expediently selected in such a way that a stopband of the desired width arises. The larger the application-related usable total spectral range, i.e. the desired width of the stopband of the filter array is to be, the larger the refractive index contrasts mentioned should be on the one hand. On the other hand, the numbers of the present layer periods 8 or 9 should be large enough for a high reflection grade and a possibly rectangular formed stopband to be obtained.

Apart from that, it is clear that the absorption of the layers 8a, 8b and 9a, 9b and the cavity sections 5a to 5d in the observed spectral ranges should be small enough, in particular if the number of the layer periods is selected large, in order to obtain, among other things, a possibly small absorption of the transmission bands.

In some cases it can finally make sense to assign to the layer 8a near the substrate 1 a thickness different from that of the other layers of the DBR mirror 3. One or more other layers could also differ in their layer thickness.

The function of the filter and sensor array described substantially results from FIGS. 1 to 4. FIG. 2 schematically indicates that the filter element 2a e.g. reflects a wavelength 14, however lets through a wavelength 11, so that it can reach the photo element 7a. However, the filter element 2d lets the wavelength 14 pass, so that it can reach filter element 7d, whereas at the same time it does not let the wavelength 11 pass. FIG. 1 shows, analogously, the transmittance spectrum of the filter array having a total of four filter elements 2a to 2d. Accordingly, the photo element 7a can only absorb radiation of the wavelength 11, the photo element 7b can only absorb radiation of the wavelength 12, the photo element 7c can only absorb radiation of the wavelength 13 and the photo element 7d can only absorb radiation of the wavelength 14, wherein the wavelengths 11 to 14 e.g. indicate the dominant wavelengths (central wavelengths) of the respective passage bands. The filter array can therefore selectively detect all four wavelengths 11 to 14.

FIG. 3 schematically shows in which way the dominant wavelength of the transmitted spectral range is determined by the geometric cavity length l, i.e. the vertical layer thickness of the cavity material. Depending on the number of waves located in cavity 5, one of the modes a, b or c is defined. Mode b, typically selected here, is e.g. characterized and selected by the stopband represented. The wavelength of the selected mode b is varied by the described thickness variation of the cavity length 1. By selecting the mirror properties and the reflecting spectrum thus determined (FIG. 3 at the bottom on the right), a selected transmission band, here only the transmission band b, comes to lie in the stopband.

FIG. 4 finally shows the transmission bands (Dips) in the dominant wavelengths 11 to 14 inside a stopband, which extends from slightly above 500 nm to slightly beneath 800 nm. In all four spectra on each ordinate the reflectivity is drawn. For clarity, the zero points are each shifted along the ordinate.

Figure 5:
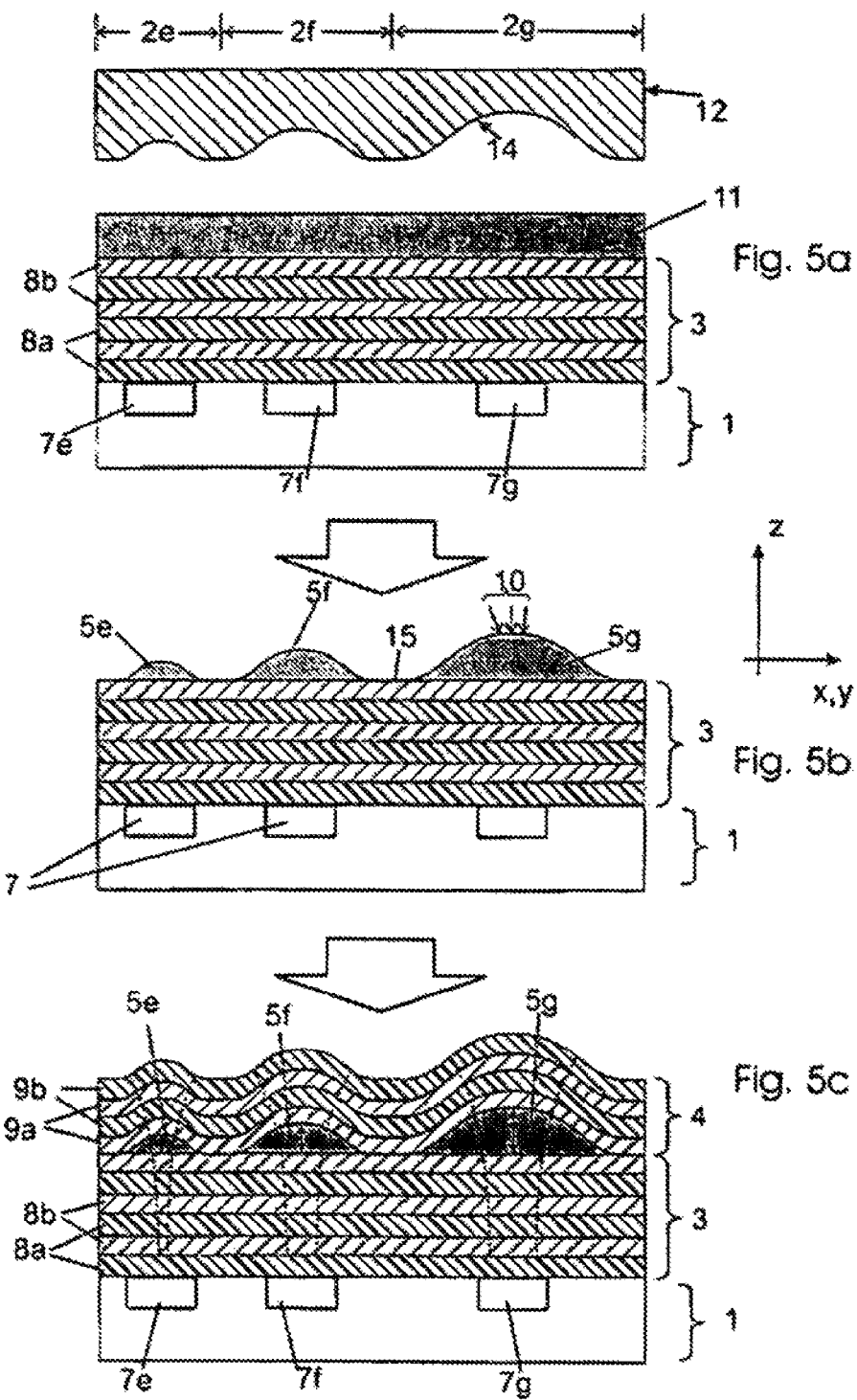

The different layer thicknesses of the cavity material in the filter elements 2a to 2d can lead to a mesa-shaped structure, which rises above a primary layer forming the separation sections 6, as shown in particular by FIG. 1. However, it is considered particularly advantageous to give a lenticular structure to the cavity sections, as represented in FIG. 5 for cavity sections 5e, 5f and 5g. These cavity sections 5e to 5g are preferably designed in such a way that for different angles of incidence of the radiation at least within a limited angle range 10 equal optical lengths are produced, as indicated in FIG. 5b for the area 10 of the cavity section 5g. It is thus possible to couple the light to be detected under different angles, without any measurement errors resulting from this.

Instead of by a thickness variation of cavity sections 5a to 5g, a variation of the optical length L can also be induced by a variation of the refractive index n. In this case, all the cavity sections 5a to 5g could have the same geometrical thickness.

The production of the optoelectronic component described is carried out with the means offered by microelectronics, optoelectronics, nanotechnology and micro system technology, it can, however, take place in various ways. The manufacturing method is subsequently explained in more detail in connection with FIGS. 5a to 5c with the help of an embodiment deemed the best so far. This procedure is such that first of all the design of the filter 2, including the respective filter elements 2a to 2d and cavity sections 5a to 5g is determined. Depending on this, if the component is to be provided with an integrated detecting device, the design of a substrate 1 containing the detecting device, which fits to the filter 2 or is adapted to the filter 2, is determined, which is e.g. a CMOS photodiode array, available e.g. in the form of a silicon chip or wafer approx. 0.5 mm thick and is provided with the photo elements 7 in the desired intervals and in the desired distribution. The substrate 1, accordingly produced, serves as a starting point for the production of the filter array. If necessary, the substrate 1 can be evened on its side facing the filter array before its application, for example, by deposition of a suitable layer or by polishing. Alternatively it is, however, also inversely possible to first of all determine the design of the substrate 1 having the detecting device or, if available in the market, to start from a present, e.g. bought substrate 1 and after that to determine a design adapted to it for the filter 2.

In a further step, a deposition of the DBR mirror 3 takes place on the substrate 1 (FIG. 5a). For this purpose, e.g. layers 8a made from silicon dioxide ($SiO_2$) and layers 8b made from silicon nitride ($Si_3N_4$) are deposited alternately with a PECVD process (Plasma Enhanced Chemical Vapor Deposition) on the substrate 1. In the simplest case, the thickness of the layers 8a is the same everywhere, and the same applies to the layers 8b, so that on the substrate 1 layer pairs 8a, 8b arise which form the DBR mirror 3, which continuously has the same thickness on the entire substrate 1.

Onto the top layer of the DBR mirror 3, a layer 11 (FIG. 5a) made of the cavity material is now applied. As the subsequent structuring of the cavity material preferably is to take place by a nanoprint process (nanoimprint process), a solid but thermally malleable material like e.g. polymethyl methacrylate (PMMA=Plexiglas) is used as a cavity material. The cavity material is applied e.g. by centrifugation like for applying photoresist, by separation or by a spray nozzle technology, wherein the layer 11 receives a continuously constant thickness.

Subsequently, the structuring of the layer 11 takes place with the help of an accordingly structured stamp 12 (FIG. 5a). Its stamping surface 14 facing the layer 11 is formed as a negative mold of the structuring to be produced in the layer 5. The structuring then takes place by heating the layer 11 to e.g. 140° C. to 160° C., in order to make the cavity material malleable, and afterward pressing the stamp 12 on it, in order to form, on the surface of the layer 11, the cavity sections represented in FIGS. 5b, 5f and 5g. The separation sections 6 according to FIG. 1 are omitted here. They are replaced here by areas 15 in which the cavity material has a thickness of almost zero. If a thickness of zero is desired here, this can be effected by e.g. additional plasma etching applied over the entire surface. Subsequent to this impression of the layer 11, the cavity sections 5e, 5f and 5g are fixed, by letting the cavity material cool down, and, where applicable, by hardening it by light irradiation, preferably by UV light.

In a last process step, the formation of the second DBR mirror 4 (FIG. 5c) takes place. This mirror 4 is applied and formed in the same way as described above for the first DBR mirror, obtaining a structuring predetermined by the cavity sections 5d to 5g, despite equal thickness everywhere. It is important to ensure that during this step the process temperature remains below the resoftening temperature of the layer 11 forming the cavity 5.

As FIG. 5c shows, a selective filter array with an integrated, photoelectronic detecting device in the form of a sensor array is obtained, which has three photo elements 7c, 7f and 7g in this embodiment, each of which is assigned to one of the filter elements 2 to 2g with the cavity sections 5 to 5g.

With the help of the technique described, filter arrays can be produced with some hundred filter elements permeable for different wavelengths. As the width of a filter dip in the exemplified wavelengths l1 to l4 is only 1 nm approx. and the width of the stopband in FIG. 4 is 280 nm approx., in this embodiment it would be possible to produce arrays with 250 to 300 filter elements approx. by variation of the thickness of the cavity material. It is assumed that the thickness variation of the cavity material from filter element to filter element needs to amount to a few nanometers only. If for the DBR mirrors 3, 4 materials are used the refractive index contrast of which is much greater than the one in the system silica/silicon nitride, stopbands with a width of e.g. 700 nm and consequently arrays with well over 500 filter elements can be produced. The cross-sections of the filter elements parallel to the imaginary xy plane amount to e.g. only a few micrometers.

The transmission bands of the filter elements can be strung together without interruption. In this case, so many filters are used until the total spectral range is covered. Alternatively the transmission bands of the filter elements, however, can also be arranged spectrally distributed, overlapping or with gaps in between. Combinations of these three cases are also possible.

In the molding techniques described for the cavity sections with the help of a stamp 12 according to FIG. 5a, numerous other cavity materials can also be used. In particular liquid, preferably viscous cavity materials can also be used, which are hardened with light or otherwise after stamping. The stamp 12 can consist of e.g. silicon, as known from the MIGA process (microstructured silicon, electroplating, impression), of metal, as known from the LIGA process (lithography, electroplating, impression) or of glass. Furthermore the structuring can take place by depositing the cavity material in the single cavity sections with different thickness on the DBR mirror 3. For this purpose, there are numerous processes. At least partially e.g. a deposition with the aid of electron, ion and/or particle radiation or electromagnetic waves or with plasma support is applicable. Applying layers of different thickness with an inkjet printing process modified accordingly is also possible.

Figure 6:
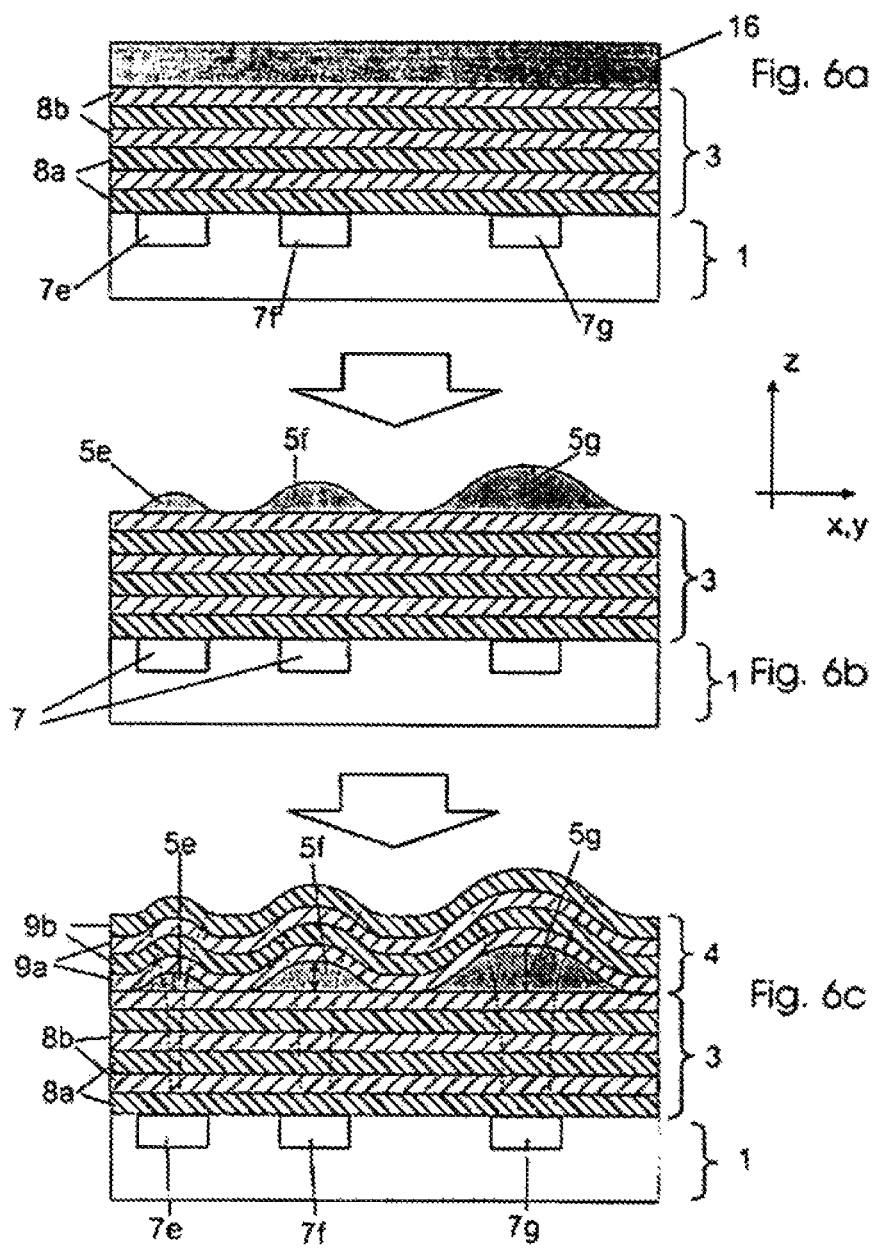

Instead of using a molding or deposition process, the structuring of the cavity material can also take place with the help of a removal process, as implied in FIGS. 6a to 6c, by e.g. locally reducing (FIG. 6b) a layer 16 of a preset thickness applied before (FIG. 6a), for example by etching or with the help of scanning probes or cantilever points. At least when applying a cavity material in the form of a polymer, it should also be borne in mind that a subsequent separation of the layers of the second DBR mirror 4, e.g. with a PECVD process from the gas phase, should take place at temperatures which lie below the glass transition temperature for the polymer. This prevents a later conversion of the polymer e.g. into a rubber-like viscous state and in this way a damage of the component or a deterioration of the optical properties of the cavity section.

The process according FIGS. 6a to 6c otherwise corresponds to the process according FIGS. 5a to 5c, for which reason for equal parts the same reference signs are used and further explanations can be dispensed with.

Finally, it is possible to provide the cavity sections, with the same geometrical thickness, with a different optical length, by varying their refractive index. Such a structuring can take place e.g. by a usual implantation process or a spatially resolved irradiation process. In this case it would be also conceivable to apply liquid or gaseous cavity materials leading to a layer of constant thickness. In all structuring processes described for the cavity material, independently of the means with which they are carried out, the predetermined position of the different photo elements 7 in the substrate 1 is of course always to be respected, if it is provided with a detecting device.

The invention is not limited to the described illustrated embodiments, which can be modified in many ways. In particular the number of filter elements available per filter array is largely arbitrary and adaptable to the desired wave range, which can extend from the UV range to the microwave range. Moreover, the processes implied for the production of the optoelectronic component only represent examples. In particular, it would be possible e.g. to produce the sensor array or the substrate 1 and the filter array separately and afterward to unite it, with exact centering of the photo elements 7a to 7g onto the filter elements 2a to 2g, by adhesion or otherwise to form a one-piece component. Moreover, the filter array is also applicable without the substrate 1 and in combination with other light processing arrays (light processing elements). Optical amplifiers, optoelectronic integrated circuits, multiplexers, demultiplexers, wavelength converters, and similar components based on wave guides are also conceivable. Moreover, photoresistor arrays, CCD arrays, photodiode arrays, phototransistor arrays and the like can also be used advantageously. In particular plastic materials are also applicable as a substrate (e.g. films, in particular flexible films made from organic materials), wherein all sorts of electronic and optoelectronic components can be integrated. All components which could be realized on inorganic basis so far are conceivable on the basis of organic materials. The elements 2 and 1 can each be used in a combined form, but also individually, and be formed as films, each of which are bent, shaped or adapted to an existing surface relief. The specified sizes of the stopbands and/or the locations of the transmission bands are only exemplified and largely depend on the geometry and the material of the DBR mirrors 3, 4 and the cavity sections. The application of the component according to the invention or that of the filter and sensor arrays is not limited to the examples implied. Further possible applications exist in sensor chips for digital and spectrometer cameras, as filter and sensor arrays for analysis purposes, in particular qualitative and quantitative analysis of the composition of gases, liquids and solids (respectively their surfaces), as well as in biotechnology or in medical technology. Each photo element (respectively each pixel) detects a preselectable wavelength. Finally, it shall understood that the different characteristics can also be used in other combinations than the ones described and represented.

FIG. 7 shows an apparatus according to the invention for the examination of the spectral and local distribution of an electromagnetic radiation indicated by arrows 1. This can be a radiation which e.g. is remitted by an object not shown, e.g. the human skin, if this object is irradiated with natural light, a lamp or otherwise.

The apparatus contains e.g. a disc, plate or foil shaped substrate 2, e.g. produced from silicon, in which a multitude of photoelectric sensor elements 3 is arranged which e.g. consist of photodiodes, phototransistors, CCD elements, photoconductors, or the like and in a manner not represented in detail are provided with electric conductor 4 in the form of conducting paths, connecting contacts, bus connectors, or the like. The lines 4 are arranged, for example, on a front side 2a of the substrate 2, in particular Vapor-deposited on them. On a back 2b of the substrate 2, however, there is a multitude of filter elements 5 receiving the radiation 1, produced in a miniaturized construction method, which are each distributed in at least one thin spectral range permeably and evenly along the back of the substrate 2. Preferably each filter element 5 is assigned to a respective sensor element 3 in such a way that radiation let through by it only impacts on the respective sensor element 3.

The sensor and filter elements 3, 5 are preferably produced by means of microelectronics, optoelectronics, nanotechnology and/or micro system technology and are therefore formed accordingly small, i.e. miniaturized. Preferably, in lateral direction, they have dimensions of no more than 100 µm, preferably of e.g. 10 µm to 20 µm, so that on a substrate 2 the broadside respectively surfaces 2a, 2b of which have a size of only a few square centimeters, without any problems a million and more pixels or pairs of sensor and filter elements 3, 5 can be accommodated. The width of a spectral range let through a filter element 5 can e.g. amount to less than one nanometer (e.g. 0.5 nm), but also to several nanometers.

FIG. 8 shows a schematic top view of a sensor according to FIG. 7, wherein each circuit implies a filter element 5. In this case, the filter elements 5 and the sensor elements 3 located among them, not visible in FIG. 8, form a sensor and filter array, in which the sensor and filter elements 5 are arranged in a Cartesian way in rows and columns.

A substantial advantage of the sensor according to FIG. 8 consists in the local and spectral resolution being able to be selected differently depending on each individual case. If, for example, all filter elements 5 visible from FIG. 8 are formed with different spectral passage bands, the entire sensor can be used as a component with a high spectral resolution. Each pixel would then deliver a different spectral information on the place at which the sensor is arranged. However, it would alternatively also be possible to subdivide the sensor into a multitude of areas or macro pixels 6a, 6b and 6c, which are exemplified in FIG. 8 and implied by contours. Each of these macropixels would then contain e.g. nine filter and sensor elements 5, 3 or subpixels. In this case, a spectral resolution which is reduced compared to the first described case corresponding to only nine respective usable spectral ranges is possible, whereas at the same time a high spatial resolution is achieved, since every single macropixel 6a, 6b and 6c delivers information on the specific place at which it is arranged.

In the example according to FIG. 8 it would be possible to assign to each macropixel 6a, 6b and 6c filter elements with the same nine spectral ranges. In this way both the possible spectral resolution and the possible spatial resolution would be determined. Grouping several macropixels would then deliver no additional spectral information. According to a particularly preferred embodiment it is therefore proposed to provide all the present filter elements 5 (subpixels) with different spectral passbands, and to distribute these spectral ranges in the sensor statistically or pseudostatistically (PRN=pseudo random noise). This means that the dominant or central wavelength does not steadily or continuous increase line by line and column by column e.g. from a sensor element 5 located in the left upper corner of FIG. 8 and having the smallest central wavelength, up to a sensor element 5 located in the right lower corner of the sensor according to FIG. 8 and having the largest central wavelength, but is distributed completely accidentally. By grouping any number of adjacent sensor elements 5 (subpixels) to form defined macro pixels, it is then possible with the same sensor to choose either a small respectively low spatial resolution and a high spectral resolution by definition of large macro pixels formed by many filter elements 5 or vice versa a high spatial resolution and a small respectively low spectral resolution by definition of comparatively small macro pixels formed by few subpixels. Grouping the filter and sensor elements 5, 3 to form macro pixels, i.e. the selection which local and which spectral resolution is used in particular cases, therefore expediently does not take place already in the original design of the sensor and filter array, but later, e.g. by purely electronic means with the help of a corresponding evaluation circuit or evaluation logic or an analysis program. Alternatively it is, of course, also possible to determine a certain number of e.g. 100 filter elements with different spectral ranges during the production of the sensor and—distributed over the sensor—to provide a multitude of macro pixels each with 100 of these subpixels. Here, too, the subpixels are distributed preferably statistically or pseudostatistically instead of evenly inside each macropixel, so that by division of these macropixels a changed spacial resolution could be provided with a similar spectral resolution. It is clear that by the formation of macro pixels from a multitude of statistically distributed subpixels no macropixels are obtained the filter elements of which have identical spectral passage bands, if the passage bands of all present filter elements are different. At least, however, macroelements with very similar filter properties are obtained, which is in fact sufficient for many application purposes. If e.g. macropixels are formed by only two subpixels each, a very high spatial resolution is reached, wherein in addition each macropixel allows at least the distinction between short and long wave radiation.

The filter arrays arranged with PRN or specifically irregularly have the following advantages.

Tuning between the mode high spectral resolution and small spatial resolution and the mode small spectral resolution and high spatial resolution is possible in a stepless way only by changing the evaluation, by composing the macropixels variably.

The spatial resolution given at the same time, in case of spectral application enables the control of the light path or path of rays or not ideal paths of rays. In a filter consisting of only one macropixel or a graduated filter or LVF (Linear Variable Filters) the uniform and geometrically unchanged illumination is necessary. If a spatial resolution is available, a variation or an inhomogeneous measuring object can be detected and, if necessary, compensated.

In the case of application to the skin or to surfaces, the spatial resolution enables the control of the correct application on the skin or on the area, since the profile of the coupling or the lighting can be defined by the spatial resolution. Thanks to the spatial resolution, information on the "evenness" of the skin area is available (absence of spots, injuries, scars, tattoos, etc.). Before the real analysis, the quality of the test area can be assessed.

In order to avail oneself of the advantages mentioned, the following requirements result.

In a transmitted light spectrometer, the requirements result from the additionally desired spatial resolution, which is used in order to detect an unstable path of rays (displacement) or inhomogeneous samples and to compensate them where applicable. In order to reach the spatial resolution, an arrangement as an array with a specific random distribution is necessary, wherein the array and the spectral range are subdivided into an equal number of parts and each part of the array contains filter elements of each spectral range. Each passband is present altogether in the same number (e.g. 1, 2, 3) on the filter array.

In a reflection spectrometer, the spatial resolution is additionally used, in order to detect an inhomogeneous surface and to compensate it where applicable, as well as to check the correct location of the measuring apparatus or the surface of the sample. In a trans reflection spectrometer, the requirements arise from the additionally desired spatial resolution, which is used in order to detect an unstable course of rays (displacement) or inhomogeneous surface or defective coupling of the measuring equipment and to compensate it where applicable, as well as to check the correct place of the measuring apparatus. In order to reach the spatial resolution, an arrangement in the form of an array with a specific random distribution is necessary. The expected spectral distribution of the light as a function of the distance between place of entry into and place of exit out of the medium (e.g. skin) has an influence on the frequency of the filter elements in a certain area of the array. Depending on the application, in the areas with very low and non-evaluable intensity of a spectral range very few or no filter elements with a corresponding passband are arranged. In the areas with a low, but still evaluable intensity of a certain spectral range, an increased number of filter elements for that very passband can increase the sensitivity of the measuring apparatus by having a larger number of filter elements available for averaging. If the light source is arranged in the middle of the array or of several arrays, this will lead to a circular arrangement of the spectral distribution areas around the light source.

Further possible embodiments of the apparatus according to the invention are illustrated in FIGS. 9 to 11. FIG. 9 shows an arrangement in which four rows $13a$ to $13d$ of filter elements 5 are present. In each row $13a$ to $13d$, starting from a preset point 8, which here is the center of the sensor, an equal number of filter elements 5 with equal spectral gradation is arranged. Rows $13a$, $13c$ and $13b$, $13d$ are arranged centrally symmetrically with respect to point 8. In this way, local and/or spectral asymmetries in the objects to be examined can be detected quickly and certainly, which could be e.g. caused by a mole on an examined skin. The same would apply if the rows $13a$ to $13d$ additionally or alternatively were arranged mirror-symmetrically (e.g. $13a$, $13d$ mirror-symmetrically to a line 9 and/or $7a$, $7b$ mirror-symmetrically to a line 10), wherein the fields $2c$ to $2f$ can also be completely occupied with filter elements.

The production of the sensor according to FIG. 9 can take place e.g. either by providing a connected substrate in the described way with sensor and filter elements 3, 5 or by using four single substrate sections $2a$ to $2d$ adjacent to one another along the lines 9 and 10, which can be formed all identically in the case of a central and mirror symmetry.

In the embodiment according to FIGS. 10 and 11, the known fact is used that in certain cases, e.g. when examining certain objects 11, such as the human skin, which is irradiated by a radiation source 14 arranged at the center of a sensor 12, parts with shorter wavelength (arrow 15) are remitted toward the sensor and filter elements 3,5 located near the center, due to the usual scattering, whereas longer wavelength portions (arrow 16) of the same light source 14 are remitted toward sensor and filter elements 3, 5 more distant from the center. In such a case, filter elements $5a$ (FIG. 11) located further inward can be provided entirely or predominantly with shortwave passage bands and filter elements $5b$ located further outward can be provided entirely or predominantly with longer wave passage bands, without a noticeable loss of information. The sensor and filter elements are arranged e.g. rotationally symmetrical with respect to the center, i.e. they are located, as FIG. 11 shows, preferably on circles with the center and the radiation source 14 as their central point. A particular advantage of the arrangement according to FIGS. 10 and 11 is also that a multitude of depth information is obtained with one measurement process. It is known that light remitted at a greater distance from the light source also penetrates up to a greater depth into the tissue or the like and therefore is absorbed by layers located deeper. For each layer, the special absorption conditions and thus e.g. defects in skin layers located deeper can therefore be determined in a simple way by taking the differences. Due to the multitude of the sensor elements present, all this information is practically received at the same time.

The sensor 12 for sensing objects 11 represented in FIGS. 10 and 11 is installed for the sensing in remission, whereas a corresponding sensor 17 represented in FIG. 12 serves for the determination of transmission spectra of an object 18. The only difference to FIGS. 10 and 5 is that the sensor 17 and a light source 19 are arranged on opposite sides of the object 18. The sensors described can of course also be arranged accordingly for the examination of fluorescence or phosphorescence spectra, as well as of scattered radiation.

FIG. 13 shows an application example as for computerized tomography. Here several sensors $20a$ to $20d$ are arranged around an object 21, which is here e.g. a human arm. The sensors $20a$ to $20d$ can be formed like the sensor 12 according to FIG. 10 and be provided each with a central radiation source $22a$ to $22d$. Alternatively or additionally, however, also radiation sources 23 from places located outside the sensors $20a$ to $20d$ can be directed to the object 21.

Instead of the Cartesian arrangement of the sensor and filter elements 3, 5 visible in FIG. 8, a polar coordinate type arrangement line by line and column by column or an arrangement in one straight or bent line only of the sensor and filter elements 3, 5 is also possible, which is not shown in detail.

The conformation of the sensor and filter elements 3, 5 can be of any kind. According to a particularly preferred embodiment, the substrate 2 according to FIG. 14, in which the same parts have the same reference signs as in FIG. 7, consists of a plane parallel flat plate, at the back $2b$ of which an optical filter is formed, which as a whole is provided with the reference sign 25. The filter 25 contains a first DBR mirror 26 applied on the back $2b$ of the substrate 2, a second DBR mirror 27, which is arranged on a side of the first DBR mirror 26 opposite to the substrate 2 and distantly from it, and a cavity provided between the two DBR mirrors 26 and 27, which is indicated in FIG. 14 as a whole with the reference sign 28. The complete sensor therefore represents a multi-layered body substantially consisting of four layers located one upon the other.

As FIG. 14 further shows, on the first DBR mirror 26 a layer made of a material forming the cavity 28 is arranged. This layer has a varying thickness parallel to z direction. In particular, the cavity 28 formed by the layer has a comparatively small thickness in a section $28a$, a slightly larger thickness in a section $28b$ and even larger thicknesses in sections $28c$ and $28d$. Geometric lengths $l_1$ to $l_4$ of the cavity 28 in these sections $28a$ to $28d$ therefore all have different values. Between the sections $28a$ to $28d$, preferably there are separating areas 29, in which the cavity material e.g. has a preset, constant, or varying thickness, and which spatially separate the sections $28a$ to $28d$ of the cavity 28 from each other.

On the layer formed by the cavity material, a zone forming the second DBR mirror 27 is situated. This zone—seen in z direction—in FIG. 14 has the same thickness everywhere. Thus the tops and bottoms of this zone have an outline or a structuring which corresponds to the upper outline or structuring of the cavity 28 in FIG. 14. The distance of the top and bottom of the DBR mirror 27 measured in z direction is substantially the same everywhere in FIG. 14.

Due to the described conformation of the cavity 28, the filter 25 in this embodiment contains four filter elements $5a$ to $5d$ corresponding to the filter elements 5 in FIG. 7, as implied in FIG. 14 by dashed lines, wherein each filter element $5a$ to 5d is formed from one of the sections 28a to 25d of the cavity 28 and from one respective section of the DBR mirrors 26 and 27. In the top view, i.e. in the xy plane, these filter elements 5a to 5d preferably have a circular shape, although they could in principle also have other peripheral contours.

The substrate 2 is preferably a film which is translucent or transmissible to the electromagnetic radiation to be detected, a thin glass plate, a silicon wafer or the like, wherein "translucent" is understood to mean that the plate does not necessarily need to be transparent in order to let through unaffected the radiation passing the filter 25, but e.g. can also have a scattering function and either be formed altogether as a diffusing panel or be provided with means scattering the radiation.

The sensor according to FIG. 14 analogously to FIG. 7 further contains a photoelectric detecting or sensor device integrated into the substrate 2, which is formed array-like. This device preferably contains one photo or sensor element 3a to 3d for each filter element 5a to 5d, e.g. in the form of a photo diode. The photo elements 3a to 3d are arranged according to FIG. 14 in the substrate 2 in such a way that they are arranged directly under those sections of the DBR mirror 26 which are assigned to a respective filter element 5a to 5d. To the filter element 5a, e.g., the photo element 3a is assigned in such a way that it can only absorb the radiation let through by filter element 5a. The same applies, mutatis mutandis, to the filter elements 5b to 5d and the respective photo elements 3b to 3d. For redundancy and other reasons it can be expedient to arrange at least two identical photo elements 3a to 3d under each filter element 5a to 5d in such a way that in case of failure of one of the two photo elements the other one remains active, and/or to arrange selected photo elements 3a to 3d at the same time under at least two different filter elements 5a to 5d, so that they respond if one and/or the other filter element lets through radiation.

The radiation-sensitive photo elements 3a to 3d in the substrate 2 closely adhere to the front side 2a or border on the front side 2a, since they currently cannot be implanted into the substrate at any depth, due to the usual production techniques, e.g. CCD or CMOS construction. With other techniques, it would be also possible, however, to let the photo elements 7a to 7d border on the back 2b, e.g. if they are formed as thermocouples. The sensor or photo elements 3a to 3d can consist of any element which is suitable for detecting radiation to the extent described here.

Finally, the substrate 2 produced e.g. in CCD or CMOS construction preferably also contains a multitude of electric or electronic components not represented, in the form of transistors and diodes or the like, by means of which the electrical signals emitted by the photo elements 7a to 7d can be processed, as well as the lines 4 also visible in FIG. 7. These lines 4 as a rule are located on the front side 2a of the substrate 2, since they are e.g. Vapor-deposited on the substrate 2, whereas the electronic components are arranged in the substrate 2. Alternatively it would, of course, also be possible to arrange only the photo elements 7a to 7d in the substrate 2, the electronic components, however, on or in a chip separate from them and, as needed, to surround them with the same or another housing.

As FIG. 14 shows, the filter 25 or its filter elements 5a to 5d are preferably formed on the back 2b of the substrate 2, which therefore forms both the substrate for the sensor device and the substrate for the filter 25. At the same time it is provided to irradiate the sensor from the back 2b facing away from the lines 4, as implied in FIG. 14 by the arrows assigned to the wavelengths l1 to l4 and in FIG. 10 by the arrows 15, 16. This ensures that the lines 4 cannot obstruct the incidence of the radiation on the photo elements 3a to 3d located below them, and/or that the lines 4 on the front 2a can be laid as desired and regardless of the location of the photo elements 3a to 3b nor of the radiation to be detected.

Since the substrate 2 is irradiated from its back 2b, i.e. the side opposite to the lines 4, and the radiation mostly has a relatively small penetration depth with respect to the substrate materials usually used, according to the invention it is further provided to make the substrate 2 sufficiently thin at least there where the filter and photo elements 5a to 5d and 3a to 3d are arranged, with a thickness of e.g. 10 m to 20 m. The sensor consists, according to FIG. 14, altogether of a filter and sensor array produced in one piece with a very small spatial expansion. It can therefore be laid onto the object to be examined at any location with its back acting as a scan area 2b and with the filter elements 5 situated on it. If using, for the cavity 28, a material which is continuously homogeneous and therefore has the same refractive index n everywhere, the cavity sections 28a to 28d have optical lengths $L1=l_1 \cdot n$, $L2=l_2 \cdot n$, $L3=l_3 \cdot n$ and $L4=l_4 \cdot n$, which differ from each other by their geometric lengths $l_1$ to $l_4$.

Unlike in FIG. 14, the described sensor with particular advantage not only contains four, but, according to the above-described description, a far larger number of e.g. at least ten, with particular advantage a hundred or more, filter elements and assigned photo elements.

The DBR mirrors 26, 27 can for the rest be designed in every way known per se (e.g. DE 103 18 767 A1).

The function of the described filter and sensor array substantially results from FIGS. 14 and 15. In FIG. 14, it is schematically indicated that the filter element 5a e.g. lets through a wavelength l1, however, reflects wavelengths l2 to l4, so that only the wavelength l1 can reach the photo element 3a. However e.g. the filter element 5d lets the wavelength l4 pass so that it can reach the filter element 3d, whereas at the same time it does not let through the wavelengths l1 to l3.

FIG. 15 shows the transmission bands (Dips) e.g. belonging to FIG. 14 in the dominant or central wavelengths l1 to l4 inside a stopband which extends from somewhat above 500 nm to somewhat below 800 nm. In all four spectra, on each ordinate the reflectivity is applied. For the sake of clarity, each zero point is shifted along the ordinate.

Instead of by a thickness variation of the cavity sections 28a to 28d, a variation of the optical length L can also be induced by a variation of the refractive index n. In this case all the cavity sections 28a to 28d could have the same geometric thickness.

The production of the optoelectronic sensor described can take place in different ways. For example, first of all the design of the filter 25 including the respective filter elements 5a to 5d and cavity sections 28a to 28d is determined, wherein the places at which filter elements with determined passbands come to lie e.g. result from a random list produced before. Depending on this fact, the design of a substrate 2 containing the detecting device, fitting to the filter 25 or adapted to the filter 25, is determined, which is e.g. a CCD or CMOS photodiode array which exists e.g. in the form of an approx. 0.5 mm thick silicon chip or silicon wafer and in the desired distances and in the desired distribution is provided with the photo elements 3. The substrate 2 produced in this way serves as a point of departure for the production of the filter array.

The substrate 2 is now, if it is not yet sufficiently thin, thinned by etching or other methods everywhere down to a thickness of e.g. 10 m to 20 m, or it is provided with a thinner center section in the area where the photo elements 3 are situated.

In a further step e.g. a deposition of the DBR mirror 26 on the back 2b of the substrate 2 takes place, e.g. by depositing alternate layers of silica ($SiO_2$) and layers of silicon nitride ($Si_3N_4$) with a PECVD process (Plasma Enhanced Chemical Vapor Deposition) on the substrate 2.

On the top layer of the DBR mirror 26, a layer of the cavity material is applied. If the subsequent structuring of the cavity material is to take place preferably by a nanoprint process, a solid but thermally malleable material such as polymethyl methacrylate (PMMA=plexiglass) is used as a cavity material. The cavity material is applied e.g. by spinning analogous to the application of photoresist, by deposition or by a spray nozzle technology.

Subsequently, the structuring of the layer consisting of the cavity material takes place, e.g. with the help of a stamp structured accordingly, the stamping surface of which, facing the layer, is formed as a negative mold of the structuring to be produced in the layer 28. The structuring then takes place by heating the layer e.g. to 140° C. to 160° C., in order to make the cavity material malleable, and afterward imprinting the stamp, in order to form the cavity sections 28a to 28d represented in FIG. 14 on the surface of the layer. Thereafter the cavity sections 28a to 28d are fixed by leaving the cavity material to cool down and possibly by hardening it by light irradiation, preferably by UV light. In a last process step, the formation of the second DBR mirror 27 then takes place in the same way as described above for the first DBR mirror 26.

With the help of the described technique, the sensors can be provided with several hundred filter elements, which are permeable to different wavelengths. As the width of a filter dip in the exemplified wavelengths l1 to l4 only amounts to approx. 1 nm and the width of the stopband in FIG. 15 amounts to approx. 280 nm, in this embodiment arrays with approx. 250 to 300 filter elements could be produced by varying the thickness of the cavity material. It is assumed that the thickness variation of the cavity material from filter element to filter element only needs to amount to a few nanometers. If for the DBR mirrors 26, 27 materials are used the refractive index contrast of which is much greater than the one in the silica/silicon nitride system, stopbands with a width of e.g. 700 nm can be produced and therefore arrays with well over 500 filter elements. The cross-sections of the filter elements parallel to the imaginary xy plane amount to e.g. a few micrometers.

The transmission bands of the filter elements can be strung together without interruption. In this case, so many filters are used until the total spectral range is covered. Alternatively, the transmission bands of the filter elements, however, can also be spectrally distributed overlapping or with gaps in between. Combinations of these three cases are also possible.

The invention is not limited to the embodiments described, which can be modified in many ways. In particular the number of filter elements per sensor is arbitrary to a great extent and adaptable to the desired wavelength range, which can extend from the UV range to the microwave range. It would also be possible to provide a sensor according to FIG. 8 with several macro pixels 6a, 6b in such a way that the filter elements of one of the macropixels have central wavelengths, which distinguish by a certain value of e.g. 1 nm from the central wavelengths of the other macropixel. Furthermore, the given process for the production of the optoelectronic component only represents an example. In particular, the substrates, as implied in FIGS. 10 and 11, can be provided with holes, which also serve for the receptacle of radiation sources in the form of light-emitting diodes, filament lamps, or fibre bundles connected to radiation sources or the like. Alternatively, such holes can also serve for e.g. the passage of daylight, as daylight can also be suitable as a light source.

Furthermore, plastic materials are also applicable as a substrate (e.g. films, in particular flexible films made from organic materials), wherein all sorts of electronic and optoelectronic components can be integrated. On the basis of organic materials, all components are also conceivable which have been realized so far on an inorganic basis. Moreover, it would be possible to produce the substrate and the filter elements separately and to connect them afterward with exact centering of the photo elements onto the filter elements by adhesive bonding or otherwise to form a one-piece component. In addition, each substrate 2 can also be bent, deviant from the dimensional form shown or adapted to an existing surface relief. The specified sizes of the stopbands and/or the locations of the transmission bands are also only exemplified and to a great extent depend on the geometry, the size and the material of the DBR mirrors 26, 27 and the cavity sections 5a to 5d. Moreover, the application of the sensor according to the invention is not limited to the indicated examples. Further possible applications consist in sensor chips for digital and spectrometer cameras, filter and sensor arrays for analysis purposes, in particular in the qualitative and quantitative analysis of the composition of gases, liquids and solids (or their surfaces) as well as in biotechnology or in medical engineering. Each photo element (or each pixel) detects a preselectable wavelength. Moreover, it is possible to provide the sensor with a protection layer on the side with which it is placed on the object to be examined, i.e. in particular on the free surface of the DBR mirror 27. It should preferably be transparent and easily washable or disinfectable and comply with the respective hygienic requirements. If this layer influences the filtering or absorption properties of the filter, this could be taken into account during the production of the filter or during the electronic adjustment of the sensitivity of the sensor. Finally, it shall be understood that the different characteristics can also be used in other combinations than the ones described and represented.

An embodiment of the present invention provides a component which, in a usual housing for e.g. socketed assembly or assembly by means of soldering incorporates the photo elements or rather the substrate with the photo elements and the filter elements or the substrate of the filter elements. In this way, not only the different filter elements of the filter are integrated into one and the same component, but also the photo elements necessary for the detection or distinction of the transmission bands or for the spectral evaluation of the radiation received absorbed. In this arrangement it is also possible to make identifiable the characteristic transmission bands and/or the spectral distribution of the radiation absorbed as well as the place where a certain radiation is emitted, simply by querying the photo elements arranged directly behind the filter elements seen in the direction of the light source, or by photo elements assigned to further optical components, i. e. without mechanical tuning of the filter.

The component, when using the method of the present invention, can be produced with relatively simple means, since the filter is directly mounted on a substrate, which is used e.g. as a window in usual housings of a detecting device produced in CMO or CCD technology. As the filter elements can also be arranged on the back of this substrate, thus in the protected interior of the element, its front side is available e.g. also for the combined installation of further optical components, such as micro lens arrays, light guides or diaphragms; moreover, the thickness of the whole or part of the substrate, also used as a window, for the filter elements can be selected in such a way that it is particularly advantageous for the function of the further optical components. Moreover, the substrate of the filter elements itself can have another optical function than that of a window, e.g. that of a bandpass filter, which is assigned to all or a spatially adjacent part of the filter elements. Due to the formation of the filter elements as Fabry Perot filters, it is also possible to accommodate, in a confined space (e.g. 1 cm×1 cm), a multitude of (e.g. several hundred) filter elements, the transmission bands of which are alternatively assigned to different or equal wavelength bands. In this way it is also possible to create a sensor which has both a high spatial resolution and a high spectral resolution.

With the presented apparatus it is possible to produce very flat, spectrally sensitive sensors. Spectrometers according to the state of the art, need a large distance—compared to the arrangement shown here—between the light access point and the photosensitive element, due to the needed spreading of the spectrum. If such a flat spectral sensitive sensor is combined with a wire or non-contact power supply and a similar data transmission in a hermetically sealed housing (FIG. 19, 1), a measuring apparatus with areas of application is obtained, which are not possible according to the state of the art. For example such a sensor unit 1 can be implanted under the skin 2. In a further unit 3, which takes over the power supply 4 and the data exchange 5 with the implanted unit, a light source 6 is integrated. If the unit with the light source is placed on the skin above the sensor unit 1, the result will be the necessary arrangement of light source, absorption path, and spectrally sensitive sensor for measuring transmission or absorption spectra. The arrangement is comparable to an arrangement (FIG. 20), in which a corresponding piece of tissue 7 is taken and introduced into the path of rays of an absorption spectrometer consisting of light source 8, monochromator 9 and detector 10. The volume between the light source unit (FIG. 19) 3 and the sensor unit 1 thus corresponds to the volume of the cuvette (FIG. 20) 11.

A measurement can be repeated any time without having to place a sensor under the skin again, i.e. without a new injury. The substantial advantage of a transmission measurement compared to a transreflective measurement or equipment (FIG. 21) 12, in which the light source 13 and light receiver or spectrometer 14 are placed on the skin 2 separated from each other by a distance or a light barrier 15, is the vertical average absorption path. Moreover, no additional shield 16 between light source and light receiver is necessary. The arrangement according to FIG. 19 guarantees that only such light reaches the receiver which has penetrated the sample, here, the skin and the underlying layers of tissue. By the position of the sensor unit, the tissue in the imaginary cuvette is identical in each measurement, by reapplying the light source unit a higher reproducibility is reached than in an equipment for transreflective measurement.

If the spectrally sensitive area of the unit (FIG. 22) 17 is provided completely or partially, which enables a reference measurement, with a layer of an indicator 18, which, e.g, reacts reversibly to the blood sugar content, by means of such an implanted sensor and a unit consisting of power supply, data transmission, and lighting as a handset, the blood sugar content can be determined any time without injury.
Basically, with the unit shown here, it is not necessary to take a sample, since the volume beamed through or the volume influencing the indicator does not have to separated or withdrawn.

If the described sensor is provided with a light source 19, a complete absorption or reflection spectrometer will arise, which can be used in a hermetically sealed housing 20 in aggressive media. This spectrometer can be e.g. introduced into the stomach and carry out continuous measurements on its way through the gastrointestinal tract. In association with a corresponding indicator it is possible e.g. to determine the pH value in the course of the gastrointestinal tract. The position of such a spectrometer is detected by the unit for power supply and data transmission. In this unit, for example, the data processing and display can also be integrated.

A corresponding sensor unit can also be provided with a data storage, which enables a precise identification and can be used for storing e.g. a patient history.

A corresponding sensor unit can deliver measured data for controlling a dosing system and, in combination with it, keep constant e.g. the insulin level. A unit for power supply and data transmission and data processing can provide dosage guidelines.

The invention claimed is:

1. A method of making an optical filter array having a first DBR mirror and a second DBR mirrors defining a cavity formed by a plurality of cavity sections having different heights and each forming a respective Fabry Perot filter element, the method comprising:
    applying the first DBR mirror to a substrate;
    applying to the first DBR mirror a layer consisting of a cavity material;
    providing a structured stamp with a stamping surface facing the cavity material, the structured stamp being formed as a negative mold of the plurality of cavity sections;
    pressing the structured stamp onto the cavity material so as to form the plurality of cavity sections and to form the respective Fabry Perot filter elements;
    at least one of fixing and hardening the plurality of cavity sections; and
    applying to the plurality of cavity sections the second DBR mirror with a structuring corresponding to the different heights of the respective plurality of cavity sections.

2. The method according to claim 1, wherein the substrate is provided with a photoelectric detecting device.

3. The method according to claim 2, further comprising the step of:
    smoothing a surface of the substrate facing the filter elements before applying the first DBR mirror to the smoothed surface.

4. The method according to claim 1, wherein the cavity material is thermally malleable, and the pressing occurs after the cavity material has been heated to a temperature of 140° C. to 160° C.

5. The method according to claim 1, wherein the cavity material is a liquid or a semifluid, and the at least one of fixing and hardening the plurality of cavity sections is provided with light irradiation.

6. The method according to claim 1, further comprising the step of:
    changing the refractive index of the layer locally with the help of an implanting method.

7. The method according to claim 1, wherein the layer is applied with a preset thickness that is then locally reduced by an abrasive process.

8. The method according to claim 1, wherein the layer is applied with a preset thickness that is then locally reduced by etching.

9. The method according to claim 1, wherein the layer is deposited on the first DBR mirror with different thicknesses.

10. The method according to claim 1, wherein the cavity material is a polymer and the deposition of the DBR mirrors takes place by deposition from a gas phase with plasma support at a temperature below a glass transition temperature of the polymer.

11. The method according to claim 1, wherein the substrate, the DBR mirrors, and the layer of the cavity material are produced separately from each other and then placed one-by-one accurately on one another.

12. The method according to claim 11, wherein the production of the substrate and the remaining parts takes place in wafer size.

13. The method according to claim 1, wherein the stamp is made by one of the following techniques: LIGA technique, MIGA technique, electron, ion, or particle beam deposition, deposition involving electromagnetic waves or deposition with plasma support.

14. The method according to claim 1, wherein the layer is applied by inkjet printing to the first DBR mirror.

15. The method according to claim 1, wherein the filter array has more than 250 filter elements.

16. The method according to claim 1, wherein the stamp is made of silicon, of a metal, or of glass.

17. The method according to claim 1, wherein the applying to the first DBR mirror the layer consisting of the cavity material occurs by centrifugation, by separation or by a spray nozzle technology.

18. An optical filter array comprising:
    a substrate permeable to electromagnetic radiation to be detected;
    a first DBR mirror and a second DBR mirror on the substrate; and
    a layer of a cavity material forming between the first and a second DBR mirrors a plurality of cavity sections that have different optical lengths and that each form with the DBR mirrors a respective filter element that has at least one respective narrow transmission band determined by an optical length of the respective cavity section and located inside a stopband of the filter array, the different thicknesses of the cavity sections being produced by:
    applying the first DBR mirror to the substrate;
    applying to the first DBR mirror the layer consisting of the cavity material;
    providing a structured stamp with a stamping surface facing the cavity material formed as a negative mold of the plurality of cavity sections;
    pressing the structured stamp onto the cavity material so as to form the plurality of cavity sections and to form respective Fabry Perot filter elements;
    at least one of fixing and hardening the plurality of cavity sections; and
    applying to the plurality of cavity sections the second DBR mirror with a structuring corresponding to the different heights of the respective plurality of cavity sections.

19. The filter array according to claim 18, further comprising:
    a detecting device constituted as CCD or CMOS circuits directly carrying the filter elements.

20. The filter array according to claim 18, wherein the cavity sections are mesa-shaped.

21. The filter array according to claim 18, wherein the cavity sections are lenticular.

22. The filter array according to claim 21, wherein the cavity sections are lenticular in such a way that they have equal optical lengths for different angles of incidence.

23. The filter array according to claim 18, wherein the cavity sections consist of a thermally malleable material.

24. The optical filter array according to claim 18, wherein the filter array has more than 250 filter elements.

25. The method according to claim 18, wherein the stamp is made of silicon, of a metal, or of glass.

26. The method according to claim 18, wherein the applying to the first DBR mirror the layer consisting of the cavity material occurs by centrifugation, by separation or by a spray nozzle technology.

27. A method of making an optical filter array having a first DBR mirror and a second DBR mirror defining a cavity formed by a plurality of cavity sections having different heights and each forming a respective Fabry Perot filter element, the method comprising:
    applying the first DBR mirror to a substrate;
    applying to the first DBR mirror a layer consisting of a cavity material as a liquid or a semifluid;
    providing a structured stamp with a stamping surface facing the cavity material, the structured stamp being formed as a negative mold of the plurality of cavity sections;
    pressing the structured stamp onto the cavity material so as to form the plurality of cavity sections and to form the respective Fabry Perot filter elements;
    hardening the plurality of cavity sections by light irradiation; and
    applying to the plurality of cavity sections the second DBR mirror with a structuring corresponding to the different heights of the respective plurality of cavity sections,
    wherein the optical filter array has more than 250 Fabry Perot elements.

* * * * *